United States Patent
Stimson et al.

(10) Patent No.: US 8,652,072 B2
(45) Date of Patent: Feb. 18, 2014

(54) KINEMATIC SYSTEM

(71) Applicants: Wendy Stimson, Los Altos, CA (US); John Caldwell, San Jose, CA (US)

(72) Inventors: Wendy Stimson, Los Altos, CA (US); John Caldwell, San Jose, CA (US)

(73) Assignee: Stimson Biokinematics, LLC, Los Altos, CA (US)

( * ) Notice: Subject to any disclaimer, the term of this patent is extended or adjusted under 35 U.S.C. 154(b) by 0 days.

(21) Appl. No.: 13/738,974

(22) Filed: Jan. 10, 2013

(65) Prior Publication Data
US 2013/0123645 A1 May 16, 2013

Related U.S. Application Data

(60) Provisional application No. 61/652,799, filed on May 29, 2012, provisional application No. 61/585,591, filed on Jan. 11, 2012.

(51) Int. Cl.
*A61B 5/103* (2006.01)
*A61B 5/117* (2006.01)
*A63B 69/00* (2006.01)
*G09B 9/00* (2006.01)
*G09B 19/00* (2006.01)
*G09B 5/00* (2006.01)

(52) U.S. Cl.
USPC .......... 600/595; 600/587; 600/594; 434/247; 434/258; 434/314

(58) Field of Classification Search
USPC .......... 600/587, 594, 595; 434/247, 255, 257, 434/258, 262, 314, 322, 324
See application file for complete search history.

(56) References Cited

U.S. PATENT DOCUMENTS

| | | | |
|---|---|---|---|
| 5,203,346 A * | 4/1993 | Fuhr et al. ............... | 600/594 |
| 5,284,345 A | 2/1994 | Jehn | |
| 5,467,992 A | 11/1995 | Harkness | |
| 6,059,576 A | 5/2000 | Brann | |
| 6,672,972 B1 | 1/2004 | Stone | |
| 6,902,493 B1 | 6/2005 | Rhodes et al. | |
| 6,939,245 B1 | 9/2005 | Mullarkey | |
| 7,131,952 B1 * | 11/2006 | Dickholtz et al. ........ | 600/594 |
| 7,207,896 B1 | 4/2007 | Sudol | |
| 7,854,668 B2 * | 12/2010 | Shelton ..................... | 473/450 |
| 7,927,252 B1 * | 4/2011 | Jeffrey ...................... | 482/8 |
| 8,043,173 B2 * | 10/2011 | Menalagha et al. ..... | 473/464 |
| 2001/0041623 A1 | 11/2001 | Rosselli | |
| 2004/0106462 A1 | 6/2004 | Ianazone | |
| 2006/0040757 A1 | 2/2006 | Rosselli | |
| 2007/0142119 A1 | 6/2007 | Popin | |
| 2007/0219025 A1 * | 9/2007 | Aberton et al. .......... | 473/450 |

(Continued)

OTHER PUBLICATIONS

PCT/US2013/021322, International Search Report and Written Opinion, Dated Mar. 13, 2013, 17 pages.

(Continued)

*Primary Examiner* — Sean Dougherty
*Assistant Examiner* — Devin Henson
(74) *Attorney, Agent, or Firm* — Blakely, Sokoloff, Taylor & Zafman LLP; Judith A. Szepesi

(57) ABSTRACT

A kinematic system is described. The kinematic system includes a kinematic device for attachment to a subject's body part. The kinematic device projects a light line, and a movement of the light line is used to evaluate a movement, posture, or balance of the subject.

21 Claims, 9 Drawing Sheets

(56) References Cited

U.S. PATENT DOCUMENTS

| | | |
|---|---|---|
| 2009/0042674 A1 | 2/2009 | Shelton |
| 2009/0047645 A1* | 2/2009 | Dibenedetto et al. ......... 434/258 |
| 2010/0076528 A1 | 3/2010 | Zeller |
| 2011/0165999 A1 | 7/2011 | Jeffrey |
| 2013/0004928 A1* | 1/2013 | Ackerman .................... 434/322 |

OTHER PUBLICATIONS

PCT/US2013/021322, International Preliminary Report on Patentability, Dated Oct. 4, 2013, 23 pages.

* cited by examiner

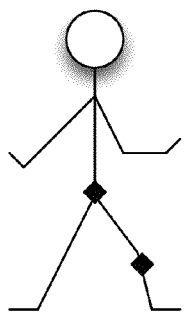
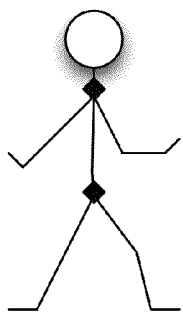
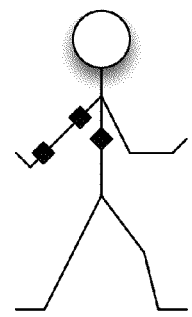
Fig. 3A  Fig. 3B  Fig. 3C
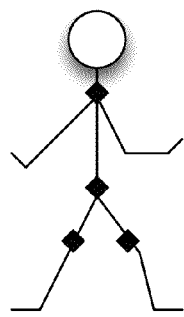
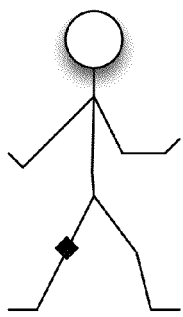
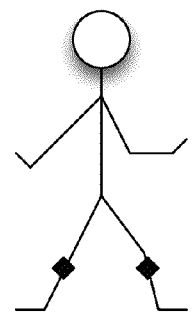
Fig. 3D  Fig. 3E  Fig. 3F

KINEMATIC SYSTEM

RELATED CASES

The present application claims priority to U.S. Provisional Application No. 61/585,591, filed on Jan. 11, 2012, and U.S. Provisional Application No. 61/652,799, filed on May 29, 2012, and incorporates both those applications by reference in their entirety.

FIELD

The present application is related to movements, and more particularly to a kinematic system to improve movement of a subject.

BACKGROUND

Human movement patterns can become disordered as a result of injury, or other causes. In general, someone whose movement has problems goes to a physical therapist. The physical therapist would attempt to explain the problem, and how to move properly to the patient. However, this can be difficult to do, and the subject may have difficulty understanding how their movement and balance should be altered. When learning to play a sport or dance, a coach generally attempts to explain how to move properly. In these cases as well, the subject may have difficulty understanding how their movement should be altered.

BRIEF DESCRIPTION OF THE FIGURES

The present invention is illustrated by way of example, and not by way of limitation, in the figures of the accompanying drawings and in which like reference numerals refer to similar elements and in which:

FIGS. 3A-3F are exemplary subjects showing various locations for the kinematic system.

DETAILED DESCRIPTION

Figure 1A:
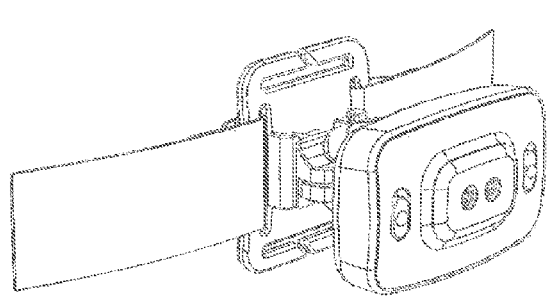
FIGS. 1A-1F are perspective views of one embodiment of a kinematic device.
Figure 1B:
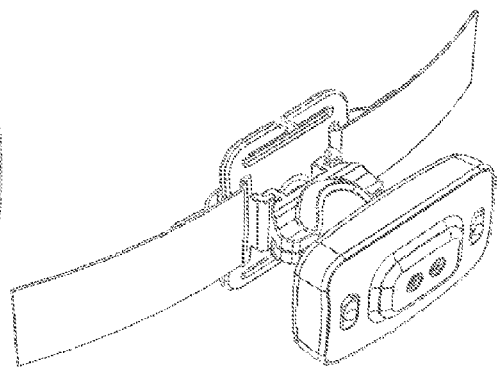
Figure 1C:
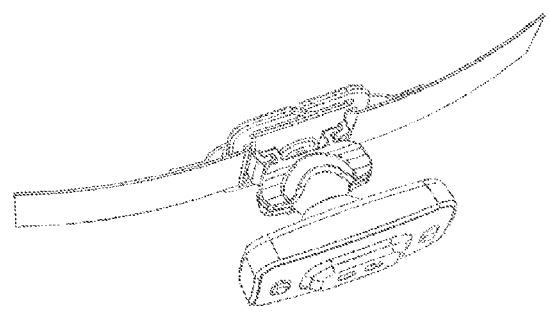
Figure 1D:
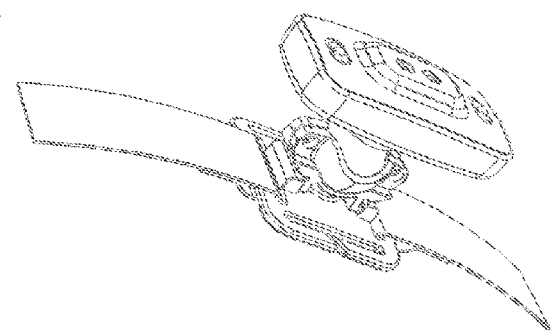

The kinematic system of the present invention enables the visualization, evaluation, and modification of human motion. The kinematic system may be especially useful for applications in health care and human performance enhancement. The kinematic system is designed to be attached to one or more body parts, and output a visual indicator that may be used for the evaluation and modification of balance, postures, and motions. The visual indication can show all planes of motion: anterior-posterior tilt, rotation, and lateral flexion. In one embodiment, the visual indication is a pair of lines, output for each relevant body part. The visual feedback, provided by movement of the line pair on an adjacent surface, can be used for evaluation and training.

This methodology can be applied to functional activities, including, but not limited to reaching, lifting, walking, ascending and descending stairs, moving from sitting to standing and standing to sitting, bed mobility, climbing a ladder, stepping to the side, and getting in and out of a car. This can be especially useful for subjects who, either due to injury or otherwise, do not properly engage their muscles or maintain proper posture and balance during these functional activities.

This methodology can also be applied to rehabilitation of a subject with an orthopedic dysfunction, including but not limited to, hyperkyphosis, cervical spine disorder, thoracic spine disorder, shoulder dysfunction, elbow dysfunction, wrist dysfunction, hand dysfunction, hip dysfunction, lumbosacral spine disorder, knee dysfunction, ankle dysfunction, and foot dysfunction. This methodology can also be applied to a subject who has had a neurologic insult, including, but not limited to brain injury, CVA, cerebral palsy, Erb's palsy, or complex regional pain syndrome. This methodology can be applied to a subject with a neurologic disorder, including, but not limited to Parkinson's disease, Parkinsonism, ataxia, dystonia, or multiple sclerosis facilitating exercises and techniques to teach controlled motion. By observing the images of the projected lines on an adjacent surface, in one embodiment the trainer and/or the subject is able to isolate motion at each joint facilitating recovery of neuromuscular recruitment strategies and optimal motor control, posture, and balance.

This methodology can further be applied to sports activities including structured movement, such as golf, tennis, walking, running, bicycling, and other activities. It can also be applied to dance, whether ballet or hip hop, and other artistic activities. Furthermore, the system may also be useful in training someone to safely and optimally perform a sequence of movements associated with the use of a machine, or performing work, such as ergonomically correct movement sequences.

The following detailed description of embodiments of the invention makes reference to the accompanying drawings in which like references indicate similar elements, showing by way of illustration specific embodiments of practicing the invention. Description of these embodiments is in sufficient detail to enable those skilled in the art to practice the invention. One skilled in the art understands that other embodiments may be utilized and that logical, mechanical, electrical, functional, and other changes may be made without departing from the scope of the present invention. The following detailed description is, therefore, not to be taken in a limiting sense, and the scope of the present invention is defined only by the appended claims.

FIGS. 1A-D are perspective views of one embodiment the kinematic system, showing two separate light outputs. In one embodiment, the separate light outputs may be associated with separate light sources, such as laser Light Emitting Diodes (LEDs). In another embodiment, it may be done with a single light emitting source, with a lens or another splitting mechanism provides two light lines, one horizontal and one vertical, on the display surface. The kinematic system is designed to project the light onto a display surface such as a wall or another flat surface onto which light may be projected.

The kinematic system has an attachment mechanism, with which the system may be attached to a body part. The attachment mechanism may include a clip, as shown, to which a strap, elastic, or other attachment mechanism is coupled. In one embodiment, the clip is integral with the body of the kinematic system. In another embodiment, the clip is separate from the body of the kinematic system, and the kinematic system has a connection that securely couples to the clip. The light output is adjustable using a multi-directional joint, which enables alignment of the light output along multiple axes of motion (up/down, right/left, and rotation), so that the projected light lines are horizontal and vertical. In the example figures shown, the multi-directional joint comprises a plurality of connections, each providing mobility along one degree of freedom (up/down, right/left, and rotation).

Although the images shown in FIGS. 1A-1D show two outputs, and a clip-based attachment mechanism, one of skill in the art would understand that the two light lines may be projected through a single aperture, and that the attachment mechanism may differ. For example, the attachment mechanism may be an integral belt, strap, clip, or other mechanism that can securely fasten the kinematic device to the subject, and the multi-directional joint may be used to connect the lens output, such that the body of the kinematic device is not moved when the light line alignment is altered.

Figure 1E:
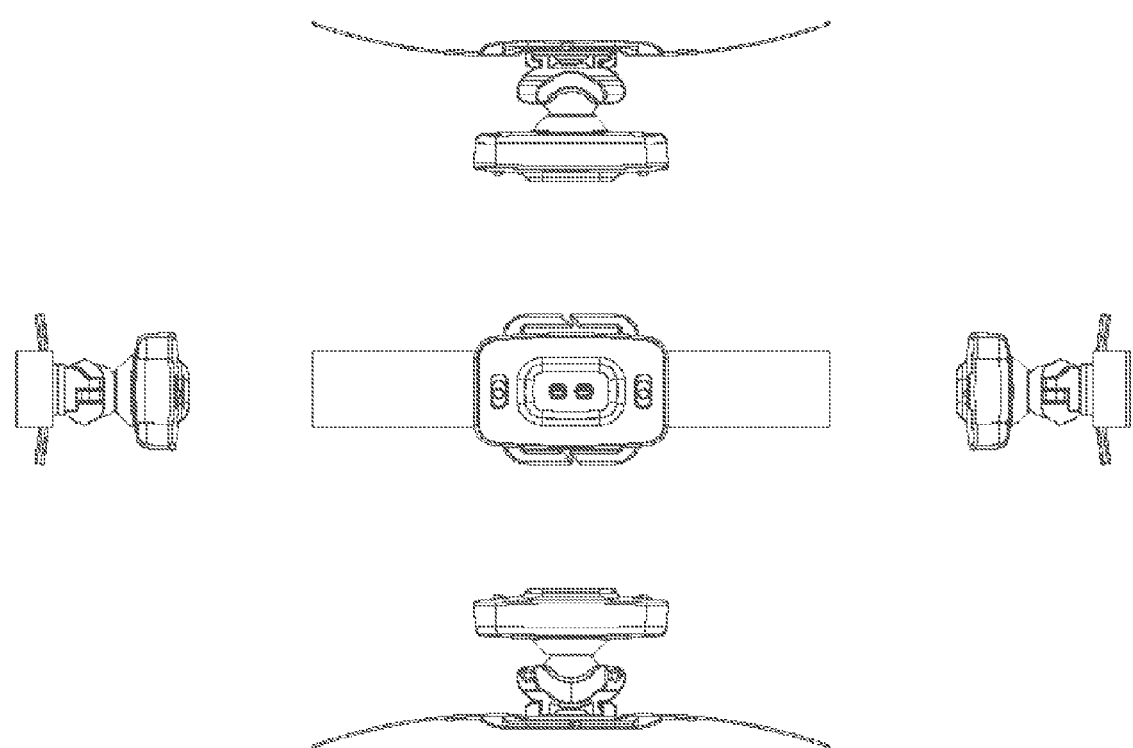

FIG. 1E illustrates an alternative configuration of the kinematic device. The system includes a clip designed to be attached to the user's body, and a kinematic device including a multi-directional joint implemented as a ball joint, which allows movement along the three degrees of freedom. However, the multi-directional joint is configured such that the device is not free-moving, but rather is fixed in place without force being applied. This enables the user or therapist to move the output of the kinematic device such that the light lines are properly aligned horizontally and vertically, without shifting the actual attachment mechanism, and maintains the alignment when the kinematic device is used.

In one embodiment, the clip is initially attached to the user's body using elastic straps, and then the kinematic device is attached to the clip. The kinematic device is then rotated on the multi-directional joint, to align the light lines, without impacting the attachment to the user's body. The use of a small clip as the stable base for the kinematic device enables the kinematic device to be attached to almost any body part securely. In one embodiment, there may be differently configured clips, for attachment to different body parts. For example, a clip is used to attach the kinematic device to the forehead may have some padding and curvature, to accommodate the body's natural shape.

Figure 1F:
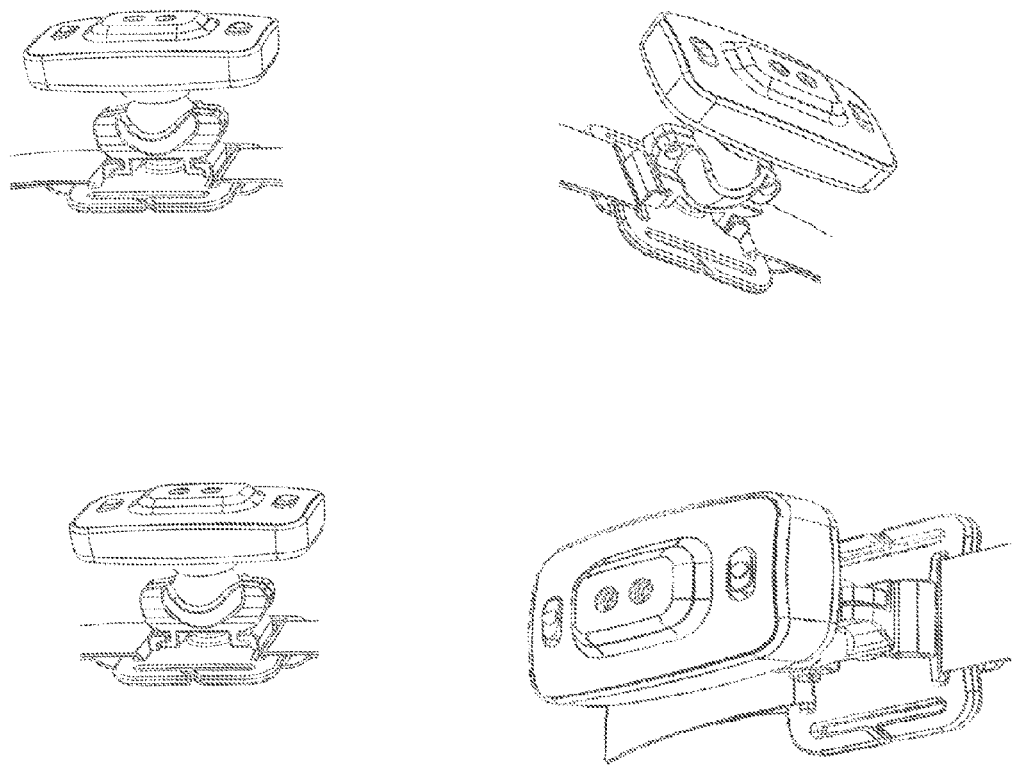

FIG. 1F illustrates another embodiment of the kinematic device, clip, and strap. As can be seen based on the various clip configurations shown in the figures, the actual configuration of the clip and multi-directional joint may vary. In one embodiment, the elastic strap, as shown, is threaded through the clip.

Figure 2:
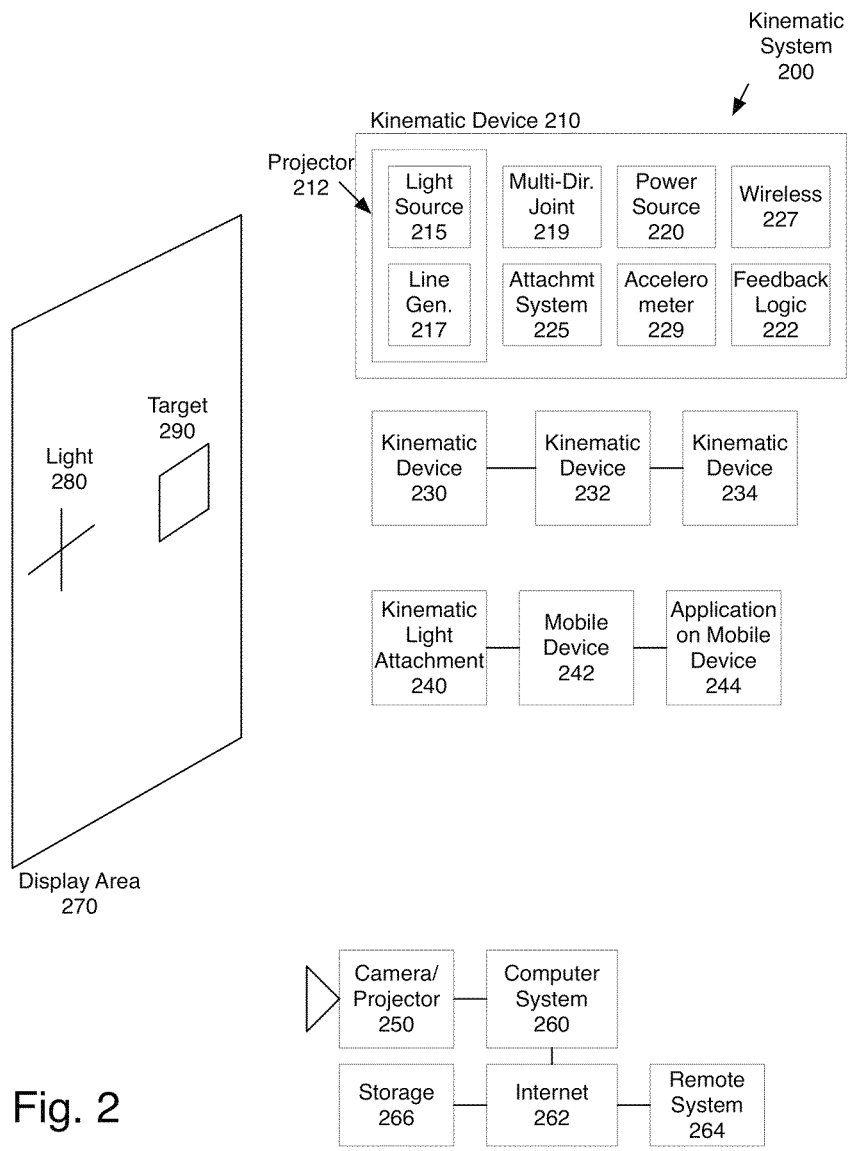
FIG. 2 is a block diagram of one embodiment of the kinematic system.

FIG. 2 is a block diagram of embodiments of the kinematic system. The kinematic device 210 includes, in one embodiment, one or more projectors 212. The projector 212, in one embodiment, includes a light source 215, such as an LED diode, and a line generator 217 that generates a line from the LED diode's light. Each projector 212 outputs in one embodiment a line of light. The kinematic device 210, in one embodiment, includes projector 212 that is designed to output a horizontal and a vertical line. In one embodiment, the horizontal line and the vertical line intersect at the center, as shown as light 280 on display area 270. Alternative configurations may include projectors 212 that display a rectangle or square shape, that display two lines which do not intersect, or that utilize another configuration for the light. However, in one embodiment, the light configuration has perpendicular lights, which are aligned with the horizontal and vertical.

In one embodiment, projector 212 is coupled via a multi-directional joint 219 to the body of the kinematic device 210. The multi-directional joint 219, in one embodiment, includes a ball joint, which acts to provide full adjustability to the projector 212, enabling alignment of the light lines output to the horizontal and vertical axis, without moving the attachment system 225 of the kinematic device 210 with respect to the user.

In another embodiment, the kinematic device is coupled to attachment system 225 via the multi-directional joint 219, such that the body of the kinematic device moves, but the attachment-portion does not. This also allows alignment of the light lines without moving the attachment system 225 of the kinematic device 210 with respect to the user's body. This enables sturdy securing of the attachment system 225, prior to aligning the light lines.

The kinematic device 210 further includes an attachment system 225. The attachment system is designed to attach the kinematic device 210 to a subject in a manner allowing the subject to move about, without losing or shifting the kinematic device 210. In one embodiment, the attachment system 225 comprises an elastic or non-elastic band and a clip. In one embodiment, the attachment system 225 comprises a clip physically molded into or coupled to the case of the kinematic device 210, and a separate elastic band or non-elastic band which is attached to the subject. In another embodiment, the attachment system 225 includes a clip that is separate from the kinematic device and a separate elastic or non-elastic band. In one embodiment, there may be a plurality of clips each having a shape adapted to be attached to a particular body part. In one embodiment, a clip for a particular body part may come in multiple sizes, to enable attachment of the kinematic device to subjects of various sizes ranging from small children to large adults. In one embodiment, the attachment system 225 is designed to be attached securely to the user, and then the other portion of the kinematic device is clicked into the clip. FIG. 4E illustrates this embodiment.

In one embodiment, the band which is attached to the subject may include an opening mechanism, such as a hook and loop closure (such as VELCRO™), a snap, a button, a hook and eye, a D-ring, a belt-loop closure, or other mechanism to enable the kinematic device 210 to be securely coupled to the appropriate body part of the subject. In one embodiment, a kinematic device 210 may be utilized with a series of different attachment mechanisms, such that different attachment mechanisms are used for different attachment locations.

In one embodiment, the kinematic device 210 further includes a power source 220. The power source 220 in one embodiment may be a rechargeable battery. In one embodiment, the power source 220 may be an alkaline, non-rechargeable battery. In one embodiment, the power source 220 may be a connection to AC power. In that instance, the kinematic device 220 may have limited range, based on the length of the power cord. Other methods of powering the system may be used.

Kinematic device 210 in one embodiment includes an accelerometer 229. Accelerometer 229 may be replaced, or supplemented, by another means of measuring movements of the kinematic device 210, such as a gyroscope, or a plurality of single axis accelerometers, or other sensors. The accelerometer 229 may be used to provide further information about the movement of the kinematic device to a user, such as a physical therapist or coach. In one embodiment, the use of the accelerometer 229 may enable interaction with a remote system, such that a remote professional may interpret the motion data, without seeing the light 280.

In one embodiment, the kinematic device 210 includes a wireless communicator 227, such as Bluetooth or Wi-Fi. This enables the kinematic device 210 to communicate with other kinematic devices (230, 230, 240), a computer system 260, and/or a remote system 264. In one embodiment, using a local area network connection such as Bluetooth or LAN, enables the kinematic device 210 to be implemented in multiple parts, to reduce the size of the portion of the kinematic device attached to the user's body.

The kinematic device 210 in one embodiment includes feedback logic 222. The feedback logic 222 provides other feedback to the user. In one embodiment, feedback logic 222 may provide sound-based feedback, voice feedback or training, visual feedback such as images showing what to do, visual feedback such as lights or other visual feedback, haptic feedback such as vibration. In one embodiment, the feedback logic 222 may also provide feedback after the kinematic device 210 was used, such that the user may review the results of the exercises done.

In one embodiment, the kinematic system 200 may include a single kinematic device 210, and a display area onto which the projector 212's output may be projected. In one embodiment, for certain exercises, described in more detail below, the display area 270 may also include a target 290. The target may be created using a marker, tape, or other mechanical implement. In one embodiment, the target 290 may be generated and projected by a computer system 260, using camera/target projector 250 or another mechanism.

In one embodiment, the kinematic system 200 comprises a plurality of kinematic devices 230, 235, 240. The kinematic devices 230, 235, 240 may be independent, or may be coupled to each other physically or via a wireless communication system. Although not shown, the kinematic devices 230, 235, 240 may include all or a subset of the elements shown for kinematic device 210. In one embodiment, the multiple kinematic devices 230, 232, 235 may be set up in a master-slave relationship. In one embodiment, when the devices are configured in the master-slave relationship, one master device may include the other elements, while the slave devices include only the projector, power source, and attachment system.

In one embodiment, the kinematic device may be implemented as a kinematic light attachment 240, which attaches to a mobile device 242 running an application 244. In one embodiment, the attachment of the kinematic light attachment 240 and the mobile device 242 may be a physical attachment. For example, the light attachment 240 may be coupled to the mobile device via a docking port. In another embodiment, the kinematic light attachment 240 may be coupled to the mobile device 242 via wireless connection. In such an embodiment, the application 244 on the mobile device 242 may be used to provide feedback, and analyze the movement of the kinematic attachment 240.

In one embodiment, the kinematic devices 210, 230, 232, 234, 240, 242, 244 may communicate with a computer system 260. The computer system 260 may include a target projector 250 to project target 290 onto display area 270. In one embodiment, computer system 260 and camera 250 may also record the light 280 and the movement of the light as the subject performs a prescribed activity. In one embodiment, the analysis described below regarding the movement may be done by computer system 260, and feedback may be provided to the subject via output from computer system 260.

In one embodiment, computer system 260 may be coupled to the Internet 262, and to a remote system 264. This enables a movement or rehabilitation professional to utilize the remote system 264 to view the subject's movements without being present in the same space. In one embodiment, the movement data may also be stored in storage 266. This would enable the professional to periodically review the subject's progress, to provide corrective instruction when needed. The corrective instruction may be provided through the computer system 260, or through other means such as a telephone or other device.

FIGS. 3A-3F are exemplary subjects showing various locations for the kinematic system. One or more kinematic devices may be attached to a subject's body. As noted above, the various locations may be associated with different clips in the attachment mechanism of the kinematic device.

FIG. 3A illustrates an example of attachment of the kinematic system to a subject. One of the kinematic devices is to the pelvis of the subject, just above the pubic bone, and shows pelvic motion in three planes, anterior/posterior tilt, pelvic rotation, and pelvic obliquity. A second kinematic device is attached to the distal femur just above the kneecap, demonstrating femoral rotation/abduction/adduction. This configuration allows for observing and correcting motion at the pelvis and the femur, which translates to hip control.

The two devices are placed on adjacent movement segments of the subject's body in one embodiment, to demonstrate motion of the joint of those segments. The two devices create and project lines on an adjacent surface to demonstrate motion. These devices can be placed on any adjacent, non-adjacent or combination moving body parts in the subject to observe and enable the correction of movements at a particular joint.

Some other configurations are shown. Although only two and four devices are shown in these exemplary configurations, one of skill in the art would understand that any number of devices, from one to N, may be used. Devices may be attached to body parts, as shown in FIG. 3A-F, such as neck, chest, elbow, wrist, waist, hip, knee, or lower leg. Additionally, the devices may be attached to other body parts not shown in FIG. 3A-F, such as head, shoulder, ankle, foot, etc. In one embodiment, anywhere between one and five such kinematic devices may be part of the kinematic system used to evaluate the motion of the subject.

Figure 4:
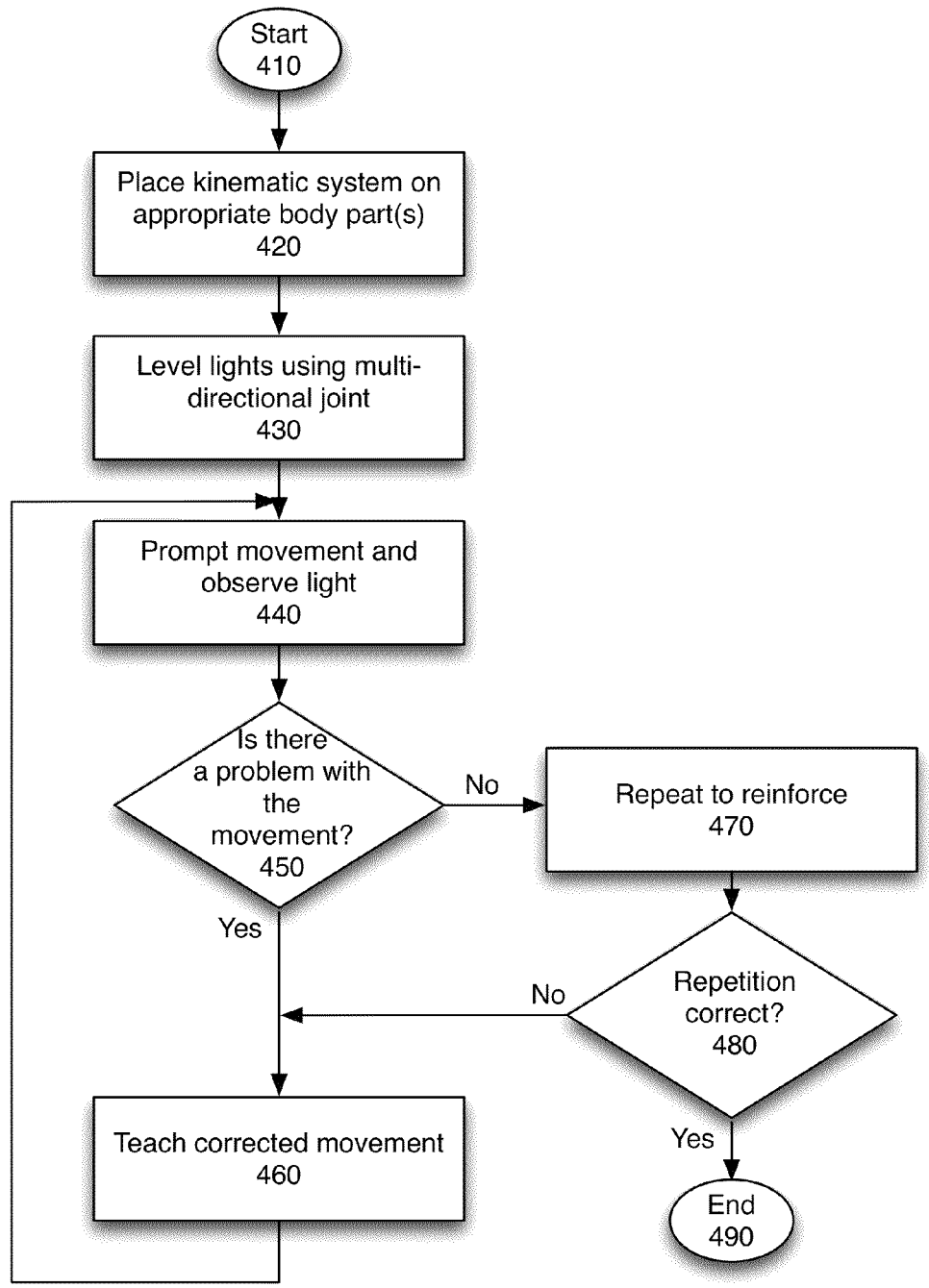
FIG. 4 is an overview flowchart of using the kinematic system.

FIG. 4 is an overview flowchart of using the kinematic system. The process starts at block 410. In one embodiment, this process is used when a subject is about to utilize the kinematic system.

At block 420, the kinematic system is placed on the appropriate body part(s). As discussed above, the selection of the body part(s) depends on which movements, postures, or aspects of balance the subject needs to correct.

At block 430, the lights are leveled, if necessary, while the subject is standing still. The leveling ensures that the horizontal line is horizontal, and/or the vertical line is vertical. This may be done manually. In one embodiment, the kinematic device's output is on a multi-directional joint, so that adjusting the light line alignment can be done by a single adjustment at the multi-directional joint, without impacting the attachment of the kinematic device to the subject's body. This enables secure attachment of the kinematic system onto a user's body regardless of the user's body shape, or which body part the kinematic device is attached to. In one embodiment, the multi-directional joint enables the light output to move freely when adjusted, but stay stable/unmoving when not being adjusted. In one embodiment, the multi-directional joint may include a locking mechanism, such that the light lines are sure not to move from their adjusted positions. In one embodiment, the multi-directional joint may be self-adjusting, with the aid of a camera or similar detection system that can determine the current configuration of the light lines, and adjust the multi-directional joint to output a vertical and horizontal light line. In one embodiment, the kinematic device may have a small motor to move the multi-directional joint until the light lines are properly aligned.

At block 440, the subject is prompted to move in the prescribed way, and the light is observed. In one embodiment, the light may also be recorded, and transmitted, by computer system.

At block 450, the process determines whether there is a problem with the movement, posture, or balance of the subject. If so, at block 460, the correct movement, posture, or balance is taught to the user, and the process returns to block 440 where the movement is prompted, and observed. In one embodiment, the correction and teaching may be done by visual feedback of the light lines showing the results of the incorrect movement, bad posture, or lack of balance. In one embodiment, the correction may be manually done by a physical therapist or other professional. In one embodiment, negative feedback is provided by a flashing red light, or other output mechanism.

If there is no problem with the movement as performed by the subject, or the subject's balance or posture, at block 470, the subject is prompted to repeat the movements to reinforce the correct movements, balance, and/or posture. In one embodiment, positive feedback is provided. For example, in one embodiment, a green light is flashed to indicate that the movement was correctly performed, the posture was good, and the balance was good. In one embodiment, a plurality of repetitions is prompted. At block 480, the process determines whether the repetitions remain correct. If so, the subject's motion is correct and no further instruction is needed. Therefore, the process ends at block 490. If the repetitions do not remain correct, the process continues to block 460 to teach the corrected movement, posture or balance.

In this way, the kinematic system may be used to teach a subject a correct set of movements to ensure that the subject utilizes the correct muscles and postural steps to take certain actions, and improve the subject's posture or balance. These actions may range from normal day-to-day actions to various sports actions, to physical therapy or rehabilitation-based actions, to training in sports movements or training in ergonomically correct motions. Two exemplary uses are described below with respect to FIGS. 5 and 6.

Figure 5:
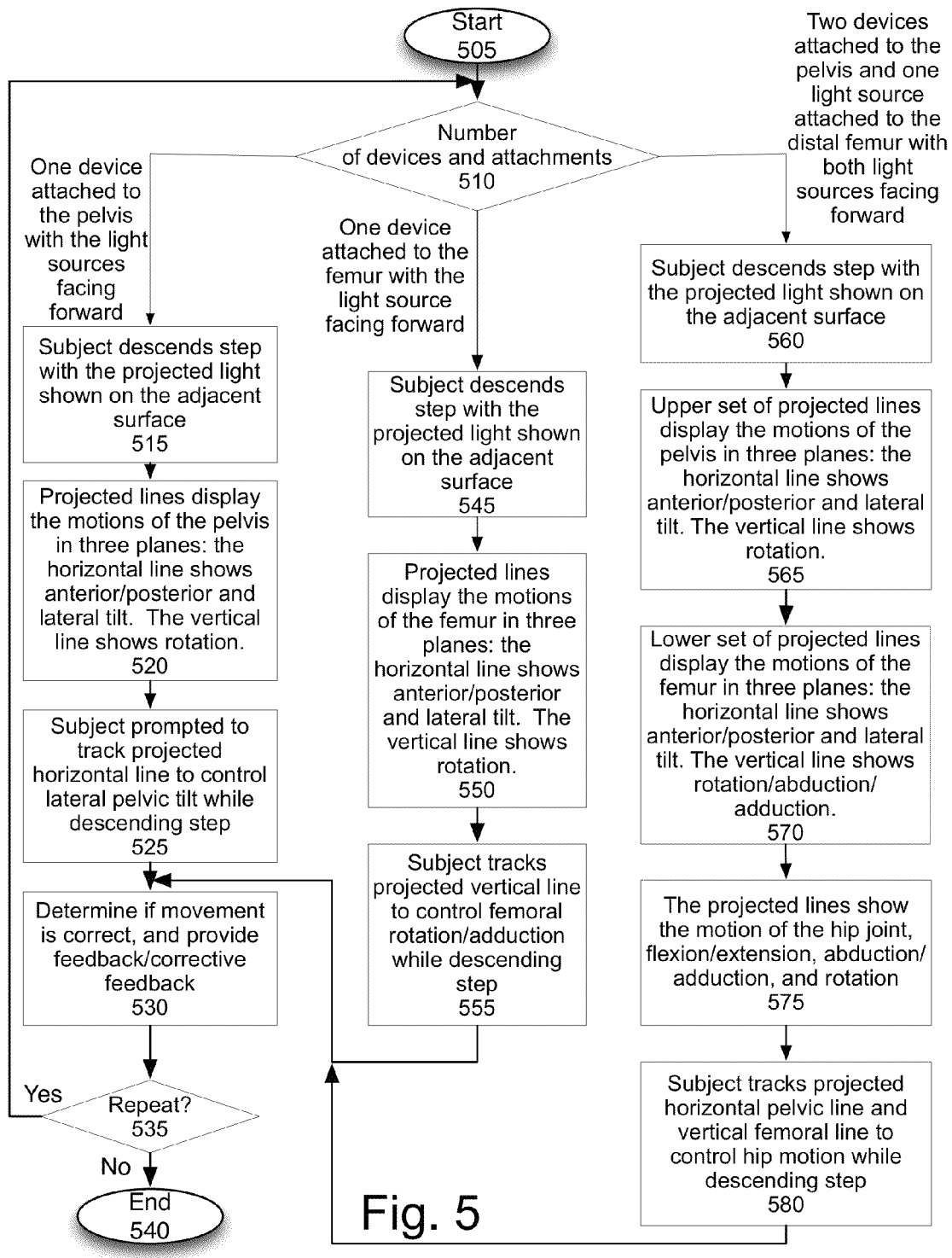
FIG. 5 is a flowchart of embodiments of using the kinematic system for stair stepping.

FIG. 5 is a flowchart of embodiments of using the kinematic system for stair stepping. The flowcharts illustrate the process with different the locations the kinematic devices attached, and the aspects that may be observed on this basis. The process starts at block 505. The flowcharts describe using a single device attached to the pelvis above the pubic bone, a single device attached to the femur, or two devices attached to the pelvis and the femur, a determined at block 510.

Pelvic motion can be observed during the ascent and descent of stairs, at block 515. One kinematic device is attached to the pelvis above the pubic bone. The subject is asked to control the horizontal or vertical tilt of the lines projected from the kinematic device attached to the pelvis to control lateral tilt of the pelvis, at block 520 and 525. In this way, the subject is able to recruit hip abductors to ascend or descend steps with better motor control. Based on an evaluation of whether the movement as correct, feedback is provided to the user. If the movement was incorrect, corrective feedback may be provided. The process determines whether the user needs to repeat the movement, at block 535, and if so returns to block 510. Otherwise, the process ends at block 540.

Recruitment of hip extension can also be encouraged with this methodology. To produce this result one kinematic device is attached to the distal femur above the kneecap. The subject is also asked to control the medial-lateral motion of the projected line while ascending and descending steps. Any medial motion of the vertical line indicates weakness or poor recruitment of the hip extensors. The subject is able to improve use of these muscles by controlling the motion of the vertical line, as described in blocks 545, 550, and 555. The process then continues to block 530 to provide feedback.

Hip motion can be demonstrated by using both of the above methodologies at the same time. The movement of the two motion segments, the pelvis and femur are illuminated on the adjacent surface and easily perceived by the subject. This method allows for assessment and correction of hip function and motor recruitment, as described in blocks 560, 565, 570, 575, and 580. The process then continues to block 530 to provide feedback.

Figure 6:
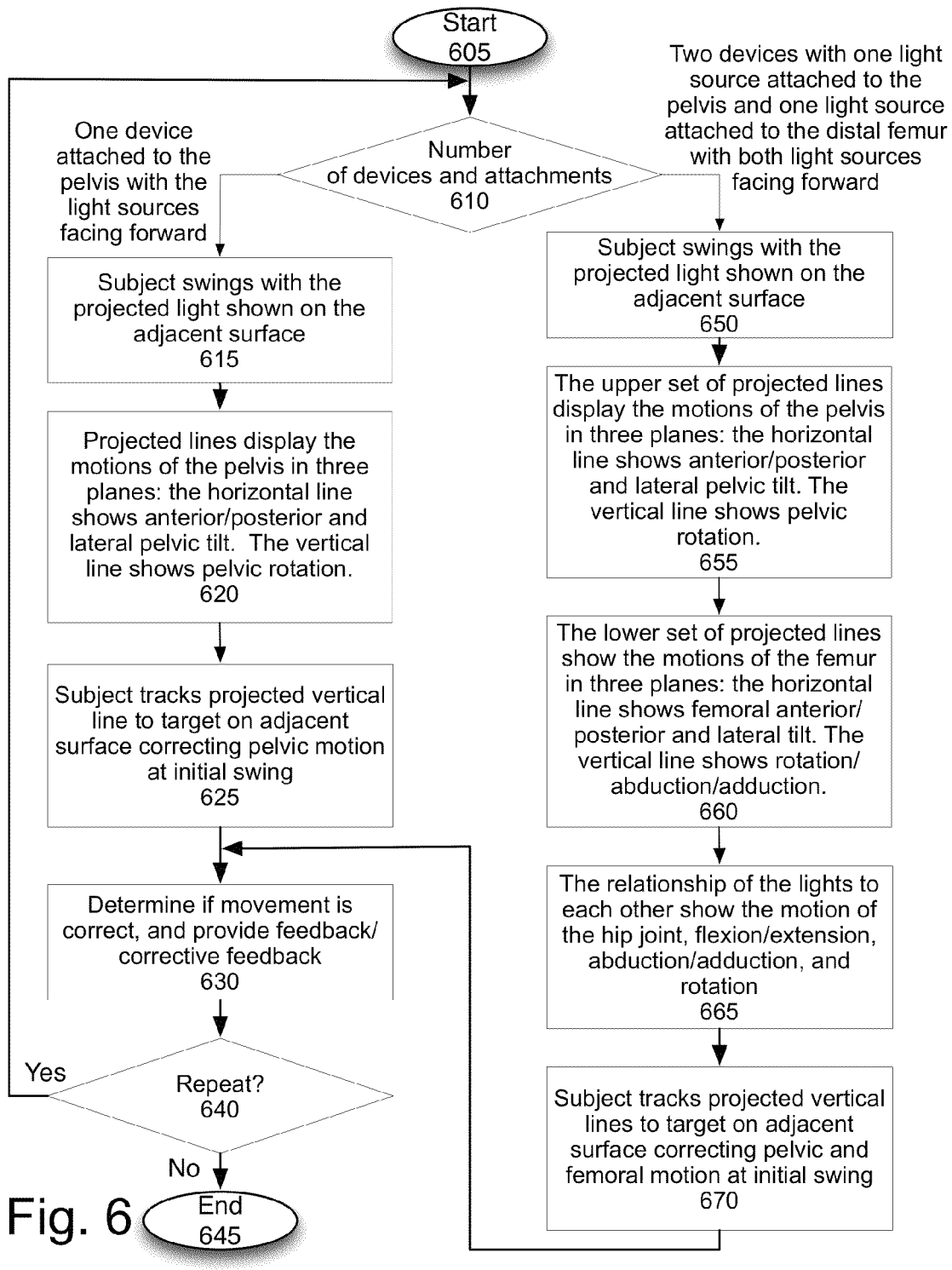
FIG. 6 is a flowchart of embodiments of using the kinematic system for golf swings.

FIG. 6 is a flowchart of two embodiments of using the kinematic system for golf swings, with two kinematic device configurations. This sport application is teaching the subject the correct 90-degree rotation of the pelvis during a golf swing from impact to follow through. The process starts at block 605. At block 610, the process determines which configuration of kinematic devices is being used.

One light emitting device is attached to the pelvis above the pubic bone, in one embodiment. For the golf swing application, the subject is asked to turn towards a target, which designates the optimum swing, at block 615. The subject is able to practice this rotation by observing the projected vertical line when turning from facing ahead, as if facing the ball, to turning 90 degrees, as if facing the hole, as described in block 620 and 625.

A target mark can be placed on, or projected on, the adjacent surface that indicates a 90-degree turn. The process determines whether the movement is correct and provides feedback. If the movement is not correct, the subject is instructed to modify the turn to reach the target with the projected vertical line. The process determines whether the movement should be repeated. If so, the process returns to block 610, otherwise the process ends at block 645. This process enables the user to learn the motor pattern, and the subject is able to repeat this movement pattern during practice and then under game conditions.

This application can be further developed by applying two light emitting devices, attaching one to the pelvis and one to the distal femur on the same side as the golf club. As described above, this application assists with developing the 90-degree rotation of the pelvis during a golf swing from impact to follow-through along with visualizing femoral motion. The projected lines in combination demonstrate hip motion. The subject is again asked to swing, aiming the kinematic device on the pelvis for the target mark that has been placed on an adjacent surface that indicates a 90 degree turn, at block 650 and 655. The subject can correct femoral motion by tracking the projected vertical line from the femoral light emitting source with the projected vertical line from the pelvic light emitting source, at block 660, 665, and 670. The subject is taught how to optimize the swing by controlling the projected vertical lines on the adjacent surface. The process then continues to block 630, to determine whether the movement is correct and provide feedback or corrective feedback.

Figure 7:
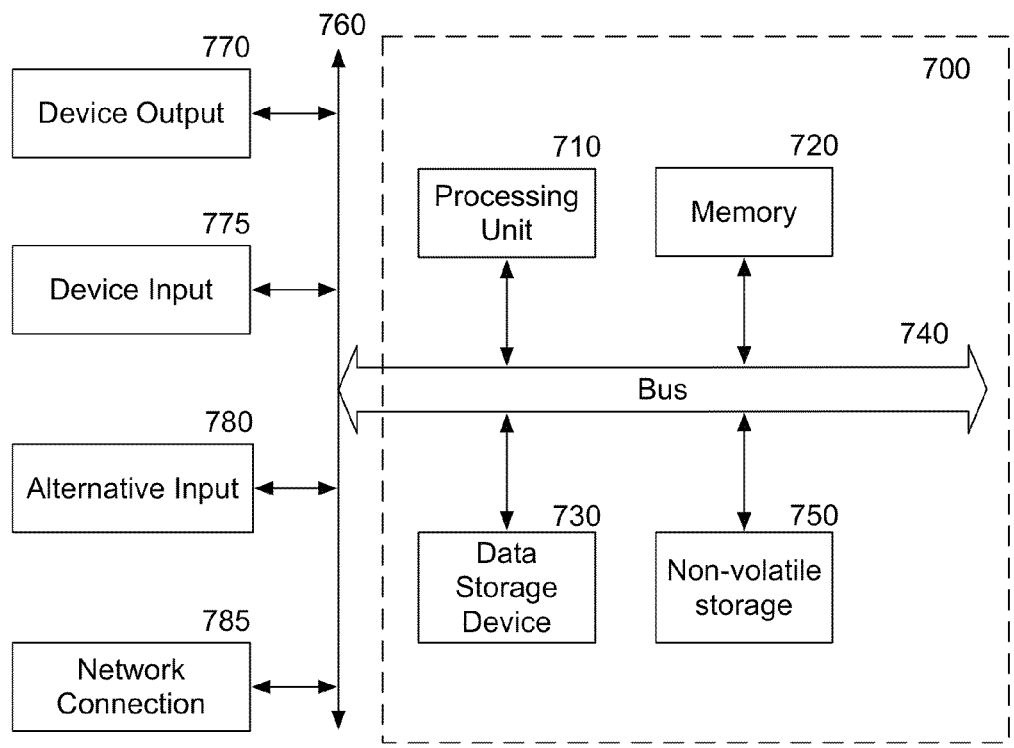
FIG. 7 is a block diagram of one embodiment of a computer system that may be used with the present invention.

FIG. 7 is a block diagram of a particular machine that may be used with the present invention. It will be apparent to those of ordinary skill in the art, however that other alternative systems of various system architectures may also be used.

The data processing system illustrated in FIG. 7 includes a bus or other internal communication means 740 for communicating information, and a processing unit 710 coupled to the bus 740 for processing information. The processing unit 710 may be a central processing unit (CPU), a digital signal processor (DSP), or another type of processing unit 710.

The system further includes, in one embodiment, a random access memory (RAM) or other volatile storage device 720 (referred to as memory), coupled to bus 740 for storing information and instructions to be executed by processor 710. Main memory 720 may also be used for storing temporary variables or other intermediate information during execution of instructions by processing unit 710.

The system also comprises in one embodiment a read only memory (ROM) 750 and/or static storage device 750 coupled to bus 740 for storing static information and instructions for processor 710. In one embodiment the system also includes a data storage device 730 such as a magnetic disk or optical disk and its corresponding disk drive, or Flash memory or other storage which is capable of storing data when no power is supplied to the system. Data storage device 730 in one embodiment is coupled to bus 740 for storing information and instructions.

The system may further be coupled to an output device 770, such as a cathode ray tube (CRT) or a liquid crystal display (LCD) coupled to bus 740 through bus 760 for outputting information. The output device 770 may be a visual output device, an audio output device, and/or tactile output device (e.g. vibrations, etc.).

An input device 775 may be coupled to the bus 760. The input device 775 may be an alphanumeric input device, such as a keyboard including alphanumeric and other keys, for enabling a user to communicate information and command selections to processing unit 710. An additional user input device 780 may further be included. One such user input device 780 is cursor control device 780, such as a mouse, a trackball, stylus, cursor direction keys, or touch screen, may be coupled to bus 740 through bus 760 for communicating direction information and command selections to processing unit 710, and for controlling movement on display device 770.

Another device, which may optionally be coupled to computer system 700, is a network device 785 for accessing other nodes of a distributed system via a network. The communication device 785 may include any of a number of commercially available networking peripheral devices such as those used for coupling to an Ethernet, token ring, Internet, or wide area network, personal area network, wireless network or other method of accessing other devices. The communication device 785 may further be a null-modem connection, or any other mechanism that provides connectivity between the computer system 700 and the outside world.

Note that any or all of the components of this system illustrated in FIG. 7 and associated hardware may be used in various embodiments of the present invention.

It will be appreciated by those of ordinary skill in the art that the particular machine which embodies the present invention may be configured in various ways according to the particular implementation. The control logic or software implementing the present invention can be stored in main memory 720, mass storage device 730, or other storage medium locally or remotely accessible to processor 710.

It will be apparent to those of ordinary skill in the art that the system, method, and process described herein can be implemented as software stored in main memory 720 or read only memory 750 and executed by processor 710. This control logic or software may also be resident on an article of manufacture comprising a computer readable medium having computer readable program code embodied therein and being readable by the mass storage device 730 and for causing the processor 710 to operate in accordance with the methods and teachings herein.

The present invention may also be embodied in a handheld or portable device containing a subset of the computer hardware components described above. For example, the handheld device may be configured to contain only the bus 715, the processor 710, and memory 750 and/or 725.

The handheld device may be configured to include a set of buttons or input signaling components with which a user may select from a set of available options. These could be considered input device #1 775 or input device #2 780. The handheld device may also be configured to include an output device 770 such as a liquid crystal display (LCD) or display element matrix for displaying information to a user of the handheld device. Conventional methods may be used to implement such a handheld device. The implementation of the present invention for such a device would be apparent to one of ordinary skill in the art given the disclosure of the present invention as provided herein.

The present invention may also be embodied in a special purpose appliance including a subset of the computer hardware components described above. For example, the appliance may include a processing unit 710, a data storage device 730, a bus 740, and memory 720, and no input/output mechanisms, or only rudimentary communications mechanisms, such as a small touch-screen that permits the user to communicate in a basic manner with the device. In general, the more special-purpose the device is, the fewer of the elements need be present for the device to function. In some devices, communications with the user may be through a touch-based screen, or similar mechanism. In one embodiment, the device may not provide any direct input/output signals, but may be configured and accessed through a website or other network-based connection through network device 785.

It will be appreciated by those of ordinary skill in the art that any configuration of the particular machine implemented as the computer system may be used according to the particular implementation. The control logic or software implementing the present invention can be stored on any machine-readable medium locally or remotely accessible to processor 710. A machine-readable medium includes any mechanism for storing information in a form readable by a machine (e.g. a computer). For example, a machine readable medium includes read-only memory (ROM), random access memory (RAM), magnetic disk storage media, optical storage media, flash memory devices, or other storage media which may be used for temporary or permanent data storage. In one embodiment, the control logic may be implemented as transmittable data, such as electrical, optical, acoustical or other forms of propagated signals (e.g. carrier waves, infrared signals, digital signals, etc.).

The present system, therefore, may be used as a stand-alone system of one or more kinematic devices utilized by a physical therapist, personal trainer, coach, rehabilitation nurse or therapist, or other skilled person. Such a person can observe the movement of the lights projected by the kinematic device, correct the subject, and ensure proper use. The kinematic system may also include a computer system, which may be a mobile system such as a smart phone or tablet computer, including a camera, which is capable of capturing and storing the data from the movements. In one embodiment, this enables a remote professional to provide coaching to the subject. In one embodiment, the computer system may provide the coaching directly, e.g. by comparing the movement of the lights to stored data indicating correct movements, and providing coaching to the subject. In one embodiment, a subject such as a neurological patient, or rehabilitation patient, who needs longer term use of the system may also utilize the kinematic devices, to ensure correct movements.

The visual data is sufficiently clear, that most users can immediately recognize and differentiate between a correct movement and an incorrect movement, once they know what the expected movement would be. The kinematic system provides immediate, clear visual feedback which is advantageous for many types of uses.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative rather than a restrictive sense.

We claim:

1. A kinematic system including a plurality of kinematic devices comprising:
    a first kinematic device comprising:
        an attachment mechanism to attach the first kinematic device securely to a subject at a first movement segment of the subject's body location, the location selected based on a type of motion of the subject to be evaluated;
        a projector to project a first light line and a second light line perpendicular to the first light line; and
        a multi-directional joint to enable a portion of the first kinematic device to move independently of the attachment mechanism, the multi-directional joint enabling an adjustment of the first kinematic device so that the first line of light is aligned along a horizontal axis and the second line of light is aligned along a vertical axis; and
    a second kinematic device for attachment to a second movement segment of the subject's body, the second kinematic device designed to project a first light line and a second light line, wherein the first and second kinematic devices demonstrate motion of one or more joints between the first and second movement segments;
    wherein movements of the subject cause movements in the first and second lines of light of the first kinematic device and the second kinematic device, the movements in the lines of light used to evaluate a movement quality of the subject showing rotation, anterior-posterior tilt, and lateral tilt at the one or more joints, based on the relationship of the movements of the lights from the first and the second kinematic device, thereby providing immediate visual feedback.

2. The kinematic system of claim 1, wherein
    the projector comprises a light source and a line generator, to generate the lines of light.

3. The kinematic system of claim 2, wherein the first line of light utilizes a first light source and the second line of light utilizes a second light source, and the projector comprising a light emitting diode (LED) and a line generator to generate the lines of light.

4. The kinematic system of claim 1, wherein the first movement segment of the subject's body is on a first side of a joint, and the second movement segment of the subject's body is on a second side of the joint, enabling a complete definition of the movements of the joint.

5. The kinematic system of claim 1, wherein the attachment mechanism comprises a clip and a strap.

6. The kinematic system of claim 5, wherein the multi-directional joint is used to attach the first kinematic device to the clip; and
    the kinematic system includes a plurality of clips having different shapes based on an intended use.

7. The kinematic system of claim 1, further comprising:
    a target projector to project a target, wherein the movements of the subject cause the first and the second lines of light to move from an original location to the target, when the movements of the subject is correctly executed to train the subject.

8. The kinematic system of claim 1, further comprising computer system configured to do one or more of:
    record the movements of the lines of light,
    communicate with a remote system to enable remote coaching,
    store the recorded data, for later review, or
    analyze the movements of the lines of light, and provide feedback to the subject.

9. The kinematic system of claim 1, further comprising an accelerometer to obtain movement data of the first kinematic device.

10. The kinematic system of claim 1, wherein the first kinematic device further comprises a wireless communication system, to enable communication between the first kinematic device and an external device.

11. The kinematic system of claim 1, further comprising:
    a feedback logic to provide additional feedback when using the kinematic system, the feedback logic providing one or more of: visual feedback, coaching feedback, speech feedback, and haptic feedback.

12. The kinematic system of claim 1, wherein the first kinematic device comprises a kinematic light attachment designed to be coupled to a mobile device and provide the first and the second lines of light, the mobile device running an application to enable analysis and feedback on the movements of the subject.

13. A kinematic system including:
    a first kinematic device comprising:
        a means for attachment enabling secure attachment of the first kinematic device at a first movement segment on a subject, the first kinematic device designed to project two light lines; and
        a means for connecting a portion of the first kinematic device in a movable manner, enabling an adjustment of an orientation of light lines projected by the first kinematic device to project a horizontal light line and a vertical light line without moving the means for attachment; and
    a second kinematic device comprising a means for attachment enabling secure attachment of the second kinematic device at a second movement segment on the subject, the second kinematic device designed to project two light lines, wherein the first and second kinematic devices demonstrate motion of one or more joints between the first and second movement segments;
    wherein upon the subject making a prescribed set of movements, movements of the light lines projected form the first and second kinematic device provide information on a movement quality of the subject showing rotation, anterior-posterior tilt, and lateral tilt of the one or more joints between the first and second movement segments, thereby providing immediate visual feedback.

14. The device of claim 13, wherein the first movement segment is adjacent to the second movement segment.

15. The kinematic system of claim 13, wherein the first kinematic device further comprises:
    a means for enabling the first kinematic device to communicate with another device, the communication to provide data about the first kinematic device.

16. The kinematic system of claim 13, further comprising:
a means for providing coaching via a computer, to the subject, wherein the coaching comprises one of: coaching communications from a remote human professional receiving movement data from the first and second kinematic devices, or coaching communications generated by a computer system based on the movement data from the first and second kinematic devices.

17. A kinematic system comprising:
a first kinematic device to be securely coupled to a first body part of a subject, the first kinematic device including a multi-directional joint to enable adjustment of the kinematic system to project a first horizontal line of light and a first vertical line of light; and
a second kinematic device to be securely coupled to a second body part of the subject, the second kinematic device to project a second horizontal line of light and second vertical line of light;
wherein when the subject performs a prescribed set of movements at one or more joints between the first and second body parts, movement of the first and the second horizontal and vertical lines of light provides visual feedback to ensure that the set of movements are correctly executed to train the subject to perform movements correctly.

18. The kinematic system of claim 17, wherein the set of movements comprises one of: movements associated with rehabilitation of the subject with an orthopedic dysfunction, rehabilitation of the subject with a neurologic insult, assistance for a subject with a neurological disorder, coaching an athlete, coaching an artist, movements associated with the use of a machine, or movements associated with performing work activities.

19. The kinematic system of claim 17, wherein the first kinematic device comprises a projector, and an accelerometer, the accelerometer enabling storage of movement data.

20. The kinematic system of claim 17, further comprising:
a target projector to project one or more targets as destinations for moving the light lines to, during the set of movements performed by the subject.

21. A kinematic system comprising:
a first kinematic device projecting a first horizontal line of light and a first vertical line of light, the first kinematic device designed to be attached to a subject at a first movement segment on a first side of a joint;
a second kinematic device to project a second horizontal line of light and second vertical line of light, the second kinematic device designed to be attached to the subject at a second movement segment on a second side of the joint;
such that when the subject moves, the projected lines provide a visual indication of the rotation, anterior-posterior tilt, and lateral tilt of the joint during motion.

* * * * *